US008568762B2

(12) United States Patent
Anitua Aldecoa et al.

(10) Patent No.: US 8,568,762 B2
(45) Date of Patent: Oct. 29, 2013

(54) METHODS FOR MODIFYING THE SURFACE OF AN IMPLANT TO PROVIDE SAID SURFACE WITH CALCIUM

(75) Inventors: Eduardo Anitua Aldecoa, Vitoria (ES); Ricardo Tejero Cantero, Vitoria (ES)

(73) Assignee: Biotechnology Institute, I Mas D, S.L., Vitoria (Alava) (ES)

( * ) Notice: Subject to any disclaimer, the term of this patent is extended or adjusted under 35 U.S.C. 154(b) by 20 days.

(21) Appl. No.: 13/233,307

(22) Filed: Sep. 15, 2011

(65) Prior Publication Data
US 2012/0071986 A1 Mar. 22, 2012

(30) Foreign Application Priority Data

Sep. 16, 2010 (ES) .................................. 201001192

(51) Int. Cl.
*A61F 2/02* (2006.01)
(52) U.S. Cl.
USPC .......................................................... 424/423
(58) Field of Classification Search
None
See application file for complete search history.

(56) References Cited

U.S. PATENT DOCUMENTS

2004/0210309 A1* 10/2004 Denzer et al. .............. 623/16.11

FOREIGN PATENT DOCUMENTS

EP 2291460 A2 * 3/2011

OTHER PUBLICATIONS

Stadlinger et al, "Surface Conditioned Dental Implants: An Animal Study in Bone Formation", J. Clin Periodontol, 36(10), 882-891, 2009.*
Stadlinger et al, "Surface Conditioned Dental Implants: An Animal Study in Bone Formation", J. Clin. Periodontal, 36(10), 882-891, 2009.*

* cited by examiner

*Primary Examiner* — Carlos Azpuru
(74) *Attorney, Agent, or Firm* — Browdy and Neimark, PLLC

(57) ABSTRACT

The invention relates to an implant for the human or animal body, which on its outer surface comprises at least one calcium salt that is soluble in a polar liquid. The invention also refers to various methods for the preparation of the preceding implant. The calcium ions contained on the surface of the implant provide said surface with four chemically and biologically advantageous properties: hydrophilicity, protection against atmospheric contamination, a pro-coagulant property and a pro-mineralising property.

4 Claims, 7 Drawing Sheets

METHODS FOR MODIFYING THE SURFACE OF AN IMPLANT TO PROVIDE SAID SURFACE WITH CALCIUM

TECHNICAL FIELD

This invention relates to an implant with a surface provided with calcium, and to a method for modifying the surface of an implant to provide said surface with calcium, the object being to achieve new chemical and biological effects in order to bring about, among other benefits, an improvement in the osseointegration of the implant in the surrounding tissue.

PRIOR ART

The process that results in the satisfactory osseointegration of an implant in the adjacent tissue is complex. Said process begins with the initiating of the coagulation cascade, the platelet aggregation and the formation of the blood clot surrounding the implant, all of which results in the creation of a matrix or provisional network of fibrin around the implant. This provisional network performs two important functions: it provides initial stability to the implant, and it provides a gradual release of platelet factors and cell markers. Among other processes, the cell markers stimulate, in this order, cellular migration to the area of the wound, their adhesion, differentiation and proliferation, and the secretion of the extracellular matrix, with its subsequent mineralisation that ends up forming the definitive bone matrix around the implant.

With regard to the surface of the implant there are three factors in particular that influence the osseointegration capacity of an implant in the adjacent tissue: firstly, the materials used to manufacture the implant are relevant; secondly, the degree of roughness of the surface of the implant is relevant; thirdly, the surface of the implant may receive treatments in order to be disposed with an additional, biologically suitable coating.

With regard to the materials used in implantology, these are considered biocompatible if their surface chemistry allows interaction with the key biological molecules in the development of the aforementioned process and in the biological tissue in question. Typically, these materials consist in titanium or titanium-based alloys, or zirconium or zirconium-based alloys. Optionally, the materials may contain additives in the form of biocompatible metals such as niobium or tantalum.

As regards the roughness of the surface of the implant, it has been shown that the provision of micro- and nano-roughness on the surface of these materials significantly increases the implant-bone connection in comparison with non-rough surfaces. There are numerous known methods for obtaining roughness, such as blasting or acid treatment (or combinations of both).

Finally, as regards the surface treatment of the implants, the prior art contains a number of known methods for the manufacture or treatment of implants in which the implant is provided with a coating that seeks to improve some of the properties of the implant, and therefore to enhance and accelerate its osseointegration and/or reduce the risk of the patient rejecting it.

These surface treatments include methods in which calcium phosphates (Ca/P) (among them, hydroxyapatite in particular) are applied on the surface of the implant in order to provide the implant with a ceramic coating similar to the mineral part of the bone. The purpose of said ceramic coating is to increase the osteoconductive properties of the implant as a means of encouraging peri-implant bone regeneration. These known methods for the application of calcium phosphates include methods in which the calcium phosphates are applied to the implant by wet means or SBF (Simulated Body Fluid, see Kim, H. M.; Miyaji, F.; Kokubo, T. & Nakamura, T. (1996): "Preparation of bioactive Ti and its alloys via simple chemical surface treatment", J Biomed Mater Res 32(3), 409-417). In these methods the implant is immersed in a solution that contains a series of ions, with Ca and P ions among them, giving rise to the precipitation of calcium phosphates on the surface of the implant. Examples of these methods by wet means or SBF can be found in EP0389713, EP1384524 and U.S. Pat. No. 6,426,114. Other methods, in which the calcium phosphates are applied on the implant by electrochemical means, are also known. In these methods, the implant is immersed in a solution that contains a series of ions, among them Ca and P ions; layers of calcium phosphate are formed on the implant in a more accelerated manner thanks to the application of electrochemical processes (see Yang, B.; Uchida, M.; Kim, H.-M.; Zhang, X. & Kokubo, T. (2004): "Preparation of bioactive titanium metal via anodic oxidation treatment", Biomaterials 25(6), 1003-1010; see Rössler, S.; Sewing, A.; Stölzel, M.; Born, R.; Scharnweber, D.; Dard, M. & Worch, H. (2003): "Electrochemically assisted deposition of thin calcium phosphate coatings at near-physiological pH and temperature", J Biomed Mater Res A 64(4), 655-663). Examples of these electrochemical methods may be found in EP1264606, U.S. Pat. No. 5,478,237, and WO2004024200. Alternatively, methods in which the calcium phosphates are applied on the implant by physical means are also known. In said methods, Ca/P precursors are sprayed on the implant by means of a plasma spray or laser (see Arias, J. L.; García-Sanz, F. J.; Mayor, M. B.; Chiussi, S.; Pou, J.; León, B. & Pérez-Amor, M. (1998): "Physicochemical properties of calcium phosphate coatings produced by pulsed laser deposition at different water vapour pressures", Biomaterials 19(10), 883-888). Examples of these methods may be found in EP0202908, EP0864332 and WO9821380. In all the aforementioned methods, the final surface finish of the implant is dry.

In addition to the foregoing, there are other methods known as implant surface conditioning methods, in which the surface properties of the implant are changed by storing the implant in diluted sodium chloride solutions (NaCl) (see, for example, document US20040210309A1) or its prior immersion in diluted sodium hydroxide (NaOH) solutions (see, for example, Stadlinger, B.; Lode, A. T.; Eckelt, U.; Range, U.; Schlottig, F.; Hefti, T. & Mai, R. (2009): "Surface-conditioned dental implants: an animal study on bone formation.", J Clin Periodontol 36(10), 882-891). In the first case the objective is to keep the implant in an environment that is free of contaminating atmospheric hydrocarbons and which maintains the original level of cleanliness. In addition, storage in an ionic liquid helps combat the hydrophobicity caused by the roughness of the surface of the implant, which enhances the wetting ability of said surface by polar liquids. In the second case the objective is to expose surface hydroxyl groups, which participate in the formation of calcium phosphates (Ca/P) on the surface of the implant once it is placed in the alveolus. This latter treatment offers improved wetting ability in relation to the unmodified one but does not prevent prior surface contamination as the immersion in the liquid takes place at the same time as it is used.

There are other treatments of the surface of implants that are based on the modification of the crystalline network of titanium by adding calcium to create calcium titanates. These are performed by the application of electrochemical or thermal methods for a specific period of time. An example of this type of treatment may be found in JP2006102212. It has been suggested that apatite forms more quickly on titanium surfaces provided with these treatments.

It is an objective of this invention to provide an alternative implant manufacturing method, in which the implant is provided with a different surface that not only offers a high surface hydrophilicity that is relatively constant in time but that also provides novel biological properties leading to optimal osseointegration and implantation of the implant in the bone and the body of the patient.

BRIEF DESCRIPTION OF THE INVENTION

It is an object of this invention to provide an implant for the human or animal body, with the specific feature that its outer surface comprises at least one calcium salt that is soluble in a polar liquid, i.e. calcium forming part of a compound with the capacity to be dissolved in a substantially immediate manner when exposed to a polar solvent (such as water, ethanol, etc). The dissolving of the calcium is equivalent to the ionising of the calcium, i.e. it is released in the form of ions from the initial compound.

As a result, the inventive implant is such that, when it comes into contact with a polar liquid, it is provided with free calcium ions on its surface. The calcium ions are capable of acting freely and to provide a series of advantageous effects that are explained at a later stage (said effects notably including a pro-coagulant action) and which have been demonstrated in tests. In contrast, in the conventional implants described, which are provided with surface calcium phosphates (Ca/P) or calcium titanates ($CaTiO_3$), the calcium is present in the form of an insoluble compound ("insoluble" being understood as any compound with a solubility in water of less than 1 g/L); this means that in conventional implants, the surface calcium is unable to be released in the environment and to interact freely. As a result, in said conventional implants calcium is not able to offer the biological functions offered by calcium in the present invention.

The polar-liquid-soluble calcium salt present on the surface of the implant may take various preferred forms. In one preferred embodiment, the calcium salt is present in a solid state (i.e. the implant has a dry surface finish or dry appearance). In another preferred embodiment, the outer surface of the implant comprises the calcium salt ions in a dissociated form, in other words, comprises the calcium salt dissolved in a polar liquid (i.e. the implant has a moist surface finish). In a third embodiment, the outer surface of the implant comprises at least one polar-liquid-soluble calcium salt in a partially dissociated state (i.e. the implant has a hydrated finish, where part of the salt ions are dissociated).

It is also an object of this invention to provide various methods for modifying the surface of an implant, to provide its surface with at least one polar-liquid-soluble calcium salt. Said methods are based on immersing, either in a temporary or permanent manner, the implant in a solution of at least one polar-liquid-soluble calcium salt. The final presentation of the implant may be dry or moist, depending on the method.

The free calcium (once dissociated from the polar-liquid-soluble calcium salt contained on the surface of the implant) provides said surface with four chemically and biologically advantageous properties: hydrophilicity, protection against atmospheric contamination, a pro-coagulant property and a pro-mineralising property.

The hydrophilic characteristic of the surface of the implant is of interest as it causes that biological polar liquids such as blood or its derivates are completely affine with the implant surface. As a result, there is an instant and equal interaction between blood or its derivates with all points of the implant surface, maximising the biological response per surface unit and the bone's capacity to form around the entire surface of the implant. This effect is especially interesting in the case of rough implant surfaces, as it overcomes the hydrophobicity caused by the roughness and enables the entire implant surface to come into contact equally with the biological medium.

Protection against atmospheric contamination is the ability of the surface of the implant to keep itself clean from external atmospheric contamination agents. Said protection stems from the fact that both the greater affinity of the titanium oxides on the surface with the calcium and the hygroscopicity of the water-soluble salts formed by the calcium generate a hydrated layer on the implant surface that prevents the hydrocarbons in the atmosphere from penetrating through to the surface of the oxide and being absorbed by said surface. As a result, the method of the present invention allows the surface of the implant to be kept free of contamination, therefore maintaining hydrophilicity over time. The method also keeps the implant in its initial clean state, which may have previously achieved affected by some known process (solvent cleaning, plasma cleaning, UV radiation cleaning).

The pro-coagulant characteristic means that the surface of the implant, which is provided with calcium in a specific range of surface concentrations, causes the activation of the coagulation cascade when it comes into contact with platelet-containing blood or blood derivatives. It is known that the free calcium ions initiate numerous processes within the coagulation cascade that lead to the formation and stabilisation of a blood clot. In fact, in the present invention, the calcium on the surface of the implant makes the implant surface resemble a repository of calcium ions.

Finally, the pro-mineralising characteristic of the surface of the implant results from the fact that the excess calcium or the calcium linked to the hydroxyls on the surface of the implant (see Ellingsen, J. E. (1991): "A study on the mechanism of protein adsorption to $TiO_2$", Biomaterials 12(6), 593-596) may act as a point of heterogeneous nucleation of the crystalline phase when there is a local increase in the supersaturation of one of the key elements in the formation of apatite: calcium.

As a result of the advantages listed above, the implant object of this invention offers the overall advantage of providing quicker and improved osseointegration. The increase in the speed of osseointegration and/or of the percentage of bone apposition around the implant object of the invention increase the chances of implantation, reduce the risk of inflammation and also reduce the waiting time for carrying out the implant's functional load.

BRIEF DESCRIPTION OF THE DRAWINGS

Details of the invention can be seen in the accompanying non-limiting drawings.

DETAILED DESCRIPTION OF THE INVENTION

Figure 1:
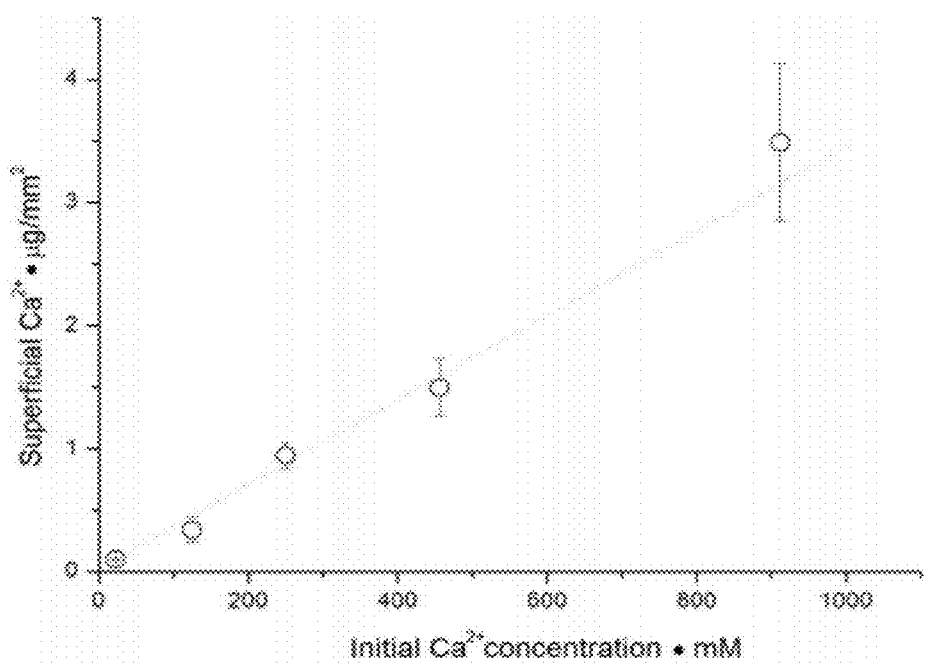
FIG. 1 shows the calcium mass (μg) per surface unit ($mm^2$) following rapid immersion (for 5 seconds) in a solution of $CaCl_2$ in ethanol at various concentrations and after drying for 1 hour vacuum conditions at 65° C., for smooth and rough surfaces.

It is an object of this invention to provide an implant whose surface comprises at least one calcium salt that is soluble in a polar liquid (hereafter, a polar-liquid-soluble calcium salt). As they form part of a soluble salt, the calcium ions become dissociated in a substantially immediate manner when exposed to a polar solvent. Subsequently, when the implant according to the invention is placed in contact with blood or plasma, the calcium ions become free (free calcium ions) and therefore capable, among other effects, of causing coagulation around the implant and of accelerating and improving the implant's osseointegration. More specifically, these free calcium ions provide the surface of the implant with at least the following biologically and chemically advantageous properties, which have been explained previously: hydrophilicity, protection against atmospheric contamination, a pro-coagulant property and a pro-mineralising property.

The implant according to the invention may be used in diverse ways: it may be placed in a hip or knee to enable the fixing of a hip or knee prosthesis; it may be placed in the jaw bone to enable the fixing of a dental prosthesis, etc.

The implant according to the invention is preferably manufactured with commercially pure titanium, titanium alloy, zirconium or mixtures of titanium and zirconium alloys. Alternatively, the implant may also contain biocompatible metallic additives, such as niobium or tantalum. The surface of the implant may be provided with macro-roughness, preferably provided by the threads of the implant itself (implants generally comprise a threaded body) or obtained with macroscopic depressions on the surface of the implant. In addition, the surface of the implant may be provided, if deemed appropriate, with additional micro- and nano-roughness superimposed on the macro-roughness. Generally, the surface micro-roughness encompasses a range of 1 to 75 µm (height from peak to trough) and preferably a range of 5 to 40 µm. The nano-roughness, superimposed on the micro-roughness, encompasses a range of 0.1 to 1 µm and preferably a range of 0.5 µm to 0.9 µm.

Furthermore, the invention comprises three methods for manufacturing or modifying the surface of the implant to provide said surface with at least one polar-liquid-soluble calcium salt. In all three methods the implant is immersed, either temporarily or permanently, in a solution of at least one polar-liquid-soluble calcium salt. Depending on the method, the final surface finish of the implant may be dry or moist.

The first method for modifying the surface of an implant according to the invention comprises the steps of immersing the implant in a solution of at least one polar-liquid-soluble calcium salt; removing the implant, with the result that a polar-liquid-soluble calcium salt is deposited on its surface; and storing the implant in a container inside which there is a dry atmosphere (a dry atmosphere being understood as an atmosphere in which there are no suspended water particles). The implant comes into contact with said dry atmosphere, with the result that the polar-liquid-soluble calcium salt remains on the surface of the implant in a solid state. The final surface finish of the implant is dry, therefore, as the surface of the implant comprises calcium salt in a solid state. The implant remains dry until it is removed from the container, at which point it tends to hydrate itself with suspended water particles, depending on the relative humidity of the environment. Given that the implant is not generally removed until immediately prior to its fitting in the patient, and that said extraction is thus carried out in the operating theatre, the implant becomes hydrated in an extremely clean environment. As a result, this dry presentation guarantees minimum contamination of the implant (by particles suspended in the air) prior to its fitting in the patient.

The dry atmosphere of the inside of the container may be achieved, for example, by maintaining the inside of the container under vacuum once the implant has been placed inside. The application of a vacuum results in the total absence of water molecules that could otherwise hydrate the coating in coordination with the calcium compound. As a result of this method, the implant surface preserved and packaged in its initial clean state. In another embodiment, the dry atmosphere is created by inserting into the container a drying agent that is more hygroscopic than the calcium of the implant surface. In this case, the dry state of the implant is preserved by means of the drying agent that absorbs the water molecules in the environment, with no need to apply a vacuum on the package. The drying agent may be silica gel, calcium chloride or calcium acetate.

The second method for modifying the surface of an implant according to the invention comprises the steps of immersing the implant in a solution of at least one polar-liquid-soluble calcium salt, removing the implant, with the result that a polar-liquid-soluble calcium salt is deposited on its surface, and storing the implant in a container inside which there is an ambient atmosphere, the implant coming into contact with said ambient atmosphere. As a result, the calcium salt remains in a solid state, unless it is a deliquescent salt such as $CaCl_2$, in which case the final surface finish of the implant is moist, i.e. the implant is hydrated either through autohydration or the deliquescence of the surface calcium deposit. In this last case, the autohydration of the implant occurs during packaging and, as a result, in conditions of maximum cleanliness. As a result of the autohydration, a film of hydrated calcium is formed, protecting the surface from potential atmospheric contaminations that could take place at a later stage.

Both methods described may comprise the additional step of drying the implant after it has been removed from the solution of at least one polar-liquid-soluble calcium salt, with the additional step of drying the implant being performed before the implant is stored. Preferably, the drying is carried out by means of one or more of the following methods: applying heat, carrying out a desiccation process and applying a vacuum. The application of heat may be performed, for example, by placing the implant in a stove at a temperature of between 50 and 150° C. for a period of between one minute and three hours (the time and the temperature depend on the hygroscopic power of the solution used and whether a vacuum is applied, which considerably reduces the stove times and temperatures). The application of a desiccation process may be performed, for example, by placing the implant in a desiccator or a container with desiccating agents that are more hygroscopic than the surface coating of the implant for a minimum period of generally ten minutes. In any of these cases, exposure to the normal atmosphere following drying must be limited to prevent surface rehydration.

The third method for modifying the surface of an implant according to the invention comprises the fundamental step of storing the implant (in a permanent manner until it is to be used) in a hermetic container that contains a solution of at least one polar-liquid-soluble calcium salt, where the concentration of the solution is between 20 and 2000 mM. The implant is stored in contact with said solution and insulated from the outside. In this case, the implant naturally has a moist final surface finish, the salt being dissociated in its ions and the calcium therefore being free. As it is immersed at all times from the packaging phase onwards, the implant is protected from external contamination.

As regards the type of solution of at least one polar-liquid-soluble calcium salt that is to be used, the first and second methods according to the invention preferably use a calcium chloride solution in any of its states of hydration in demineralised water or in ethanol or, alternatively, a calcium acetate solution in any of its states of hydration in demineralised water. These calcium salts are preferred due to their high solubility in water: in excess of 60 g/100 mL at ambient temperature in the case of calcium chloride and in excess of 30 g/100 mL in the case of calcium acetate, which means that in the concentrations in question, the ions of these salts are completely dissociated. The calcium chloride solution in ethanol is useful because it enhances the wetting ability of the surface to be treated, as the ethanol has less surface tension than the water. In this method, the implant in its final state prior to its application comprises calcium chloride or calcium acetate hydrate (with water molecules), regardless of the type of solvent used (demineralised water or ethanol). As a result, in the event that the solvent is ethanol, the ethanol evaporates and, in normal conditions, is replaced by atmospheric water until the hydration limit of the excess calcium deposit on the surface is reached. This hydration limit is dictated by the relative humidity of the environment. Greater or smaller levels of hydration do not affect the effective amount of calcium on the surface of the implant, which is determined the retention of calcium during the process of immersion in the calcium solution and which increases with the calcium concentration of the base solution and the available surface (see Test 1). The immersion time must be at least 5 seconds to ensure that the entire surface of the implant is evenly covered with calcium.

In the third method according to the invention, a solution of calcium chloride in any of its states of hydration in demineralised water is preferably used or, alternatively, a solution of calcium acetate in any of its states of hydration in demineralised water. The solution of calcium chloride in ethanol, which may be used in the first and second methods, is not used in this third method. This is because, as the implant is stored in a solution, the wetting ability of the entire surface of the implant is already guaranteed and, in the event of ethanol being used, the clinical process would be delayed until the ethanol evaporated (once having removed the implant from the container) and the ionised calcium became rehydrated with atmospheric water particles. It must be taken into account that installing the implant while its surface still contains ethanol is not suitable as the ethanol has an anti-coagulating effect on blood.

For the first and second methods, the concentration of the solution of at least one polar-liquid-soluble calcium salt is preferably comprised between 20 and 2000 mM, while for the third method the concentration of the solution necessarily lies within this range. This range ensures that the implant offers the aforementioned hydrophilicity properties, protection against atmospheric contamination and a pro-mineralising property, as shown by the experiments detailed below. To ensure that the implant also offers pro-coagulant properties, the concentration of the solution of at least one polar-liquid-soluble calcium salt must be between 100 and 1000 mM, as has also been shown in tests.

As well as having a surface that is hydrophilic, protected against atmospheric contamination, pro-coagulant and pro-mineralising, the implant according to the invention offers an additional advantage that is explained in detail below.

As is known, the surface of a titanium dental implant is a polar surface, as it comprises $O^-$ and $OH^-$ ions along with surface titanium oxides. When the implant is fitted in the patient, the polar surface of the implant comes into contact with the bloodstream. As is known, a large number of hydro-soluble biomolecules present in the patient, which participate in the bone-generating processes and which possess electrical charges, are potentially attracted to the polar surface of the implant. In particular, it is known that free calcium $Ca^{2+}$ ions present in the bloodstream (approximately 0.4 mg/mL; see Ellingsen J E, 1991 Biomaterials) end up forming electro-static bonds with the negative charges of the surface of the implant and that said electro-static bonds are very helpful in the medium and long post-implantation term, encouraging the osseointegration of the implant. Specifically, the $Ca^{2+}$ ions of the $OH^-$—$Ca^{2+}$ electro-static bonds cause the adsorption of $H_xPO_4^{3-x}$ from the biological environment, encouraging the formation of calcium phosphate phases, which are bone precursors. In addition, the calcium is capable of attracting many proteins with acidic residues (negatively charged) that participate in the bone regeneration process by means of specific calcium-binding mechanisms. In short, the success of titanium as a biomaterial is attributable to the fact that its bond with the calcium present in blood is the fundamental basis of the mechanism for the adsorption of proteins to its surface (to its oxides) and of the subsequent processes that lead to osseointegration.

By means of the present invention, having a titanium oxide surface exposed beforehand (before coming into contact with the patient) to solutions with calcium ions implies that part of this calcium is bound in an electro-static manner to the partially negative charges of the surface before coming into contact with the patient. As a result, full use is made of the potential of the surface to adsorb $Ca^{2+}$ ions (improved adsorption performance per surface unit) as the surface has not been the object of atmospheric contamination.

In general, the surface of the implant that is the object of this invention enables quicker and better osseointegration for two reasons: firstly, due to the immediate availability of surface calcium ions; secondly, due to the larger number of surface calcium ions capable of acting as nucleation points of the crystalline phase, thanks to the fact that virtually all the OH groups of the surface of the implant are used. As a result, the invention allows that the processes initiated by the calcium occur since the very initial post-implantation moments and that a quicker and higher-quality peri-implant bone regeneration is obtained.

The method according to the invention also has differences and different effects in relation to conventional methods in which the implant is stored in diluted solutions of sodium chloride (NaCl) or sodium hydroxide (NaOH). In all methods, the hydrophobicity of the implant is eliminated due to the implant roughness (by releasing the air retained in the roughness) and the implant is protected from contact with certain atmospheric hydrocarbons (except in the case referred to in Stadlinger B, 2009 J Clin Periodontol, as, in this case, the implant is immersed immediately before its use, instead of being preserved or stored in a solution, or with a protective layer, as in the present invention), resulting in the surface being cleaner. However, in said conventional methods the implant is stored in NaCl or NaOH, with have no biological activity inside the coagulation cascade (as will be seen from the detailed explanation of FIG. 5), whereas in the implant according to the invention the two aforementioned advantageous effects are achieved: firstly, the previous binding of calcium ions to the hydroxyl groups of the surface of the implant, which encourages biomineralization and the formation of the definitive matrix around the implant, i.e. osseointegration; secondly, the excess calcium not bound to the surface hydroxyls of the implant is released to provide its own advantages (to initiate the coagulation process and the formation of the provisional matrix during the initial post-insertion period, etc). The qualities of the implant according to the invention are also present from the very first moment and at the places of greatest clinical importance, i.e. in the bone-implant interphase.

Furthermore, with regard to the method described in patent WO0224243A1 (which describes the surface treatment of an implant by means of its successive bathing in different acids, followed by neutralisation, washing and the application of Plasma Rich in Growth Factors, PRGF) improvements are made in clinical applicability as the PRGF does not need to be activated with calcium chloride but is activated merely on coming into contact with the surface of the implant, as the implant according to the invention is already provided with calcium salts that are soluble in the PRGF.

Experimental Results

A series of experiments are detailed below, the results of which showed that the surface of the implant according to the invention does indeed possess hydrophilicity, protection against atmospheric contamination, and pro-coagulant and a pro-mineralising properties, all of which are mentioned throughout this document. In addition, in a subsequent experiment, the mineralising ability of the surface was studied and the ability of the calcium coatings to form apatite in comparison with non-coated surfaces was tested (i.e. the pro-mineralising characteristic of the surface was tested). Finally, a cytotoxicity study was carried out, allowing any negative effect of these coatings on osteoblastic cells to be ruled out (i.e. it was found that the inventive coating allows the correct adhesion of osteoblastic cells on the implant to take place).

Said experiments are the following:
Test 1: Bases for the calculation of the amount of surface calcium.
Test 2: Topographical characterisation and compositional analysis.
Test 3: Hydrophilicity and protection against contamination.
Test 4: Pro-coagulant characteristic.
Test 5: Pro-mineralising characteristic.
Test 6: Cytotoxicity.

Test 1: Bases for the Calculation of the Amount of Surface Calcium

1. Objective

The objective of the first test was to determine the amount of calcium carried away per surface unit according to the following parameters: the fact that the $CaCl_2$ solution uses demineralised water or ethanol as a solvent; the $CaCl_2$ concentration of said solution.

2. Materials and Methods

All the reactives used were obtained from Scharlab S. L., Barcelona, Spain.

The surfaces of the implants were prepared. Implants with a roughness of Sa=0.7 μm and Sdr=35% were used. Said implants were ultrasound-washed with Triton X-100, acetone and ethanol, for 20 minutes. Five implants were used for each of the base solution concentrations.

The solutions were prepared. Dihydrate calcium chloride $CaCl_2.2H_2O$ ($CaCl_2$) was used as a solute. 95 wt. % Ethanol and demineralised water were used as a solvent. The solution concentrations ranged from 28 to 912 mM.

A rapid immersion was then carried out and titrations performed. Specifically, the implants were exposed to a rapid immersion (5 seconds) in vials that contained 1 mL of various solutions of calcium chloride. The implants were then removed and placed in vials with 1 mL of water. After five hours, the contents of each vial (implant+water) were deposited in an Erlenmeyer. One mL of water was then added to the vial four times and then to the Erlenmeyer to wash away the entire contents of the vial. The implant remained immersed during the titration. EDTA 0.05M was used as a titrating agent, adjusted to a pH of 11 with NaOH 2M. Murexide was used as an indicator.

After rapid immersion, the implants were then dried, being exposed to 65° C. in a vacuum stove for 1 hour.

3. Results and Discussion 3.1 Selection of the Solvent

TABLE 1

Breakdown of the amount of calcium carried away per surface unit as a percentage according to the solvent used

| | Solvent | | |
|---|---|---|---|
| | Water | Ethanol | Ethanol and drying |
| Average variation coefficient (%) | 16.91 | 13.30 | 13.15 |

The prior tests ascertaining the amount of calcium carried away by the surfaces according to the type of solvent used showed that when the calcium is dissolved in ethanol it generates coatings with less dispersion in the value of surface calcium than is the case when the calcium is dissolved in water (Table 1). This is due to the fact that, as ethanol is a liquid with less surface tension than water, the soaking of the entire rough surface in rapid immersion is more homogeneous. In the case of $CaCl_2$ in ethanol but without drying, it may occur that the ethanol does not evaporate completely, giving rise to partial rehydration with water. As a means of achieving greater reproducibility, therefore, the method involving rapid immersion in $CaCl_2$ in ethanol and subsequent drying was chosen.

3.2 Amount of Calcium Carried Away Per Surface Unit

FIG. 1 shows the relationship between the amount of surface calcium and the initial calcium concentration of the solutions with which the implants are treated (the figure specifically shows the calcium mass (µg) per surface unit ($mm^2$) following rapid immersion (5 seconds) in a solution of $CaCl_2$ in ethanol at different concentrations and following drying for 1 hour at 65° C. and under vacuum, for rough surfaces). The use of ethanol as a solvent means the deviations on each value are minimal.

The surface loading coefficient deduced from a linear regression of the data obtained is $3.4\pm3$ ng·$mm^{-2}$·$mM^{-1}$.

The results of the following tests are expressed according to the amount of surface calcium calculated with this coefficient and not from the initial concentrations of the $CaCl_2$ solution.

Test 2: Topographical Characterisation and Compositional Analysis

1. Objective

The objective of this test is to evaluate the morphology of the calcium-coated surface and determine its composition before and after being exposed to immersion in a polar liquid.

2. Materials and Methods

All the reactives used were obtained from Scharlab S. L., Barcelona, Spain.

The implant surfaces were prepared using discs with a diameter of 6 mm, a height of 3 mm and a roughness of Sa=0.7 µm and Sdr=35%. Said discs were ultrasound-washed with Triton X-100, acetone and ethanol, for 20 minutes.

The solutions were prepared. $CaCl_2.2H_2O$ (dihydrate) was used as a solute. 95 wt. % Ethanol was used as a solvent.

To create the coatings, the equivalent volume was deposited to that carried away by similar implant surfaces in order to provide a final concentration of 2.4 µg/$mm^2$.

The discs were then dried, being exposed to 65° C. in a vacuum stove for 1 hour following coating with the solutions. The discs exposed to washing were also immersed three times in demineralised water and allowed to air-dry.

The samples were analysed using a JEOL JSM-5500LV scanning electron microscope (Akishima City, Tokyo, Japan) and an Oxford Inca 300 energy-dispersive spectrometer (EDS) (Witney, Oxon, UK), which enables the detection of elements situated above carbon (included) in the periodic table. The images were taken at an acceleration voltage of 20 kV.

3. Results and Discussion 3.1 Morphology of the Coatings

Figure 2:
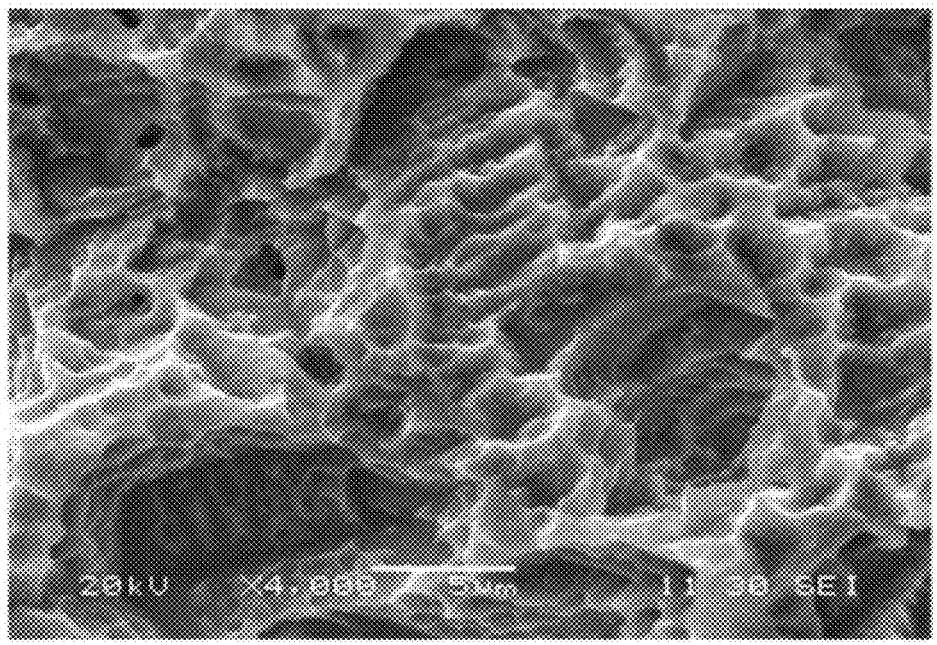
FIG. 2 shows a micrograph obtained by a scanning electron microscope on a rough surface without a calcium coating.
Figure 3:
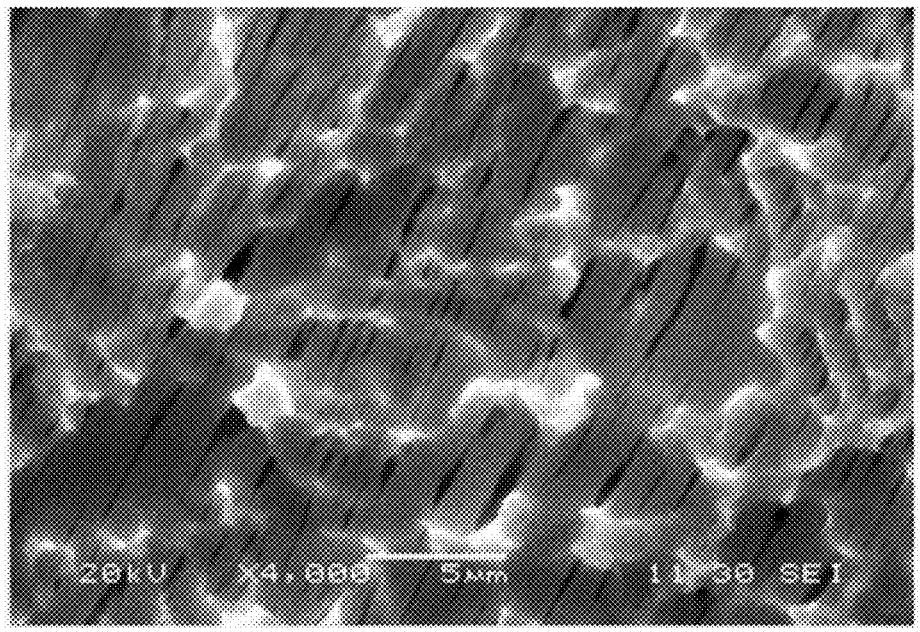
FIG. 3 shows a micrograph obtained by a scanning electron microscope on a rough surface with a calcium coating of 2.4 μg/$mm^2$.
Figure 4:
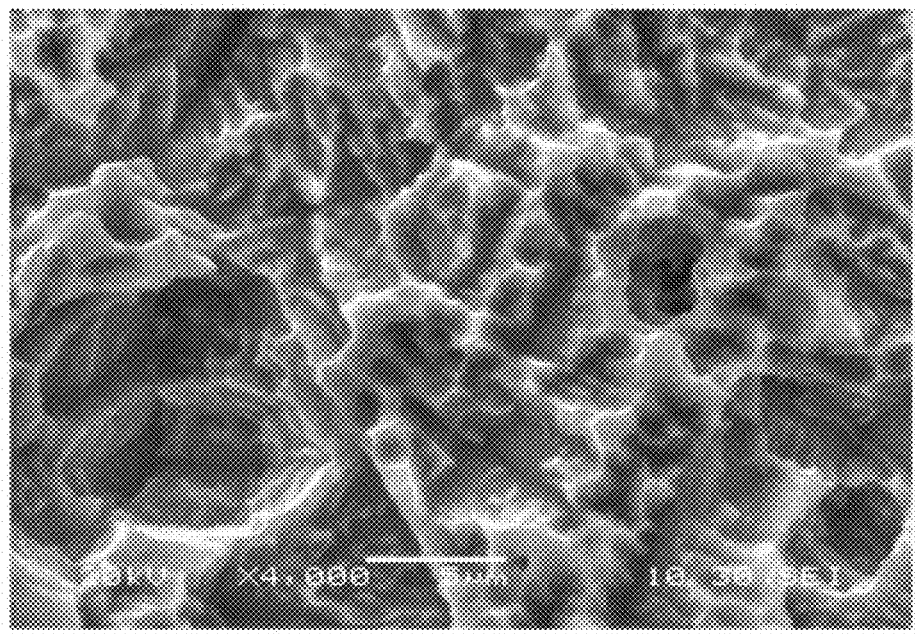
FIG. 4 shows a micrograph obtained by a scanning electron microscope on a rough surface with a calcium coating of 2.4 µg/mm² after immersing the surface in a polar liquid.

Unlike the non-coated discs (FIG. 2), a layer on the underlying rough surface can be seen on the calcium-coated discs (FIG. 3). As the surface is washed in demineralised water, it can be seen that the calcium coating appears to have disappeared (FIG. 4), presumably dissolved in the polar medium in which it has been treated. This is the desired effect in the event of it coming into contact with blood or plasma (see Test 4).

3.2 Analysis of Elements

Figure 6:
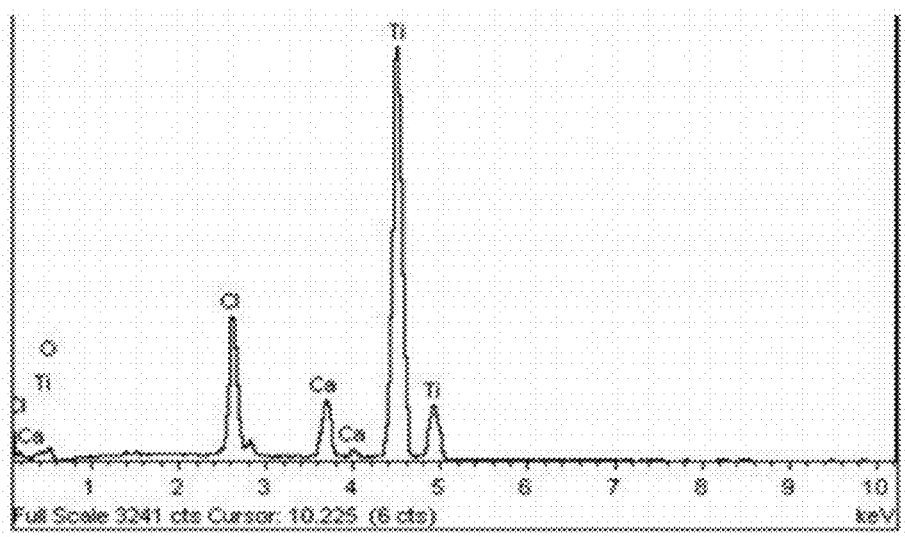
FIG. 6 shows the dispersion spectrum obtained from a rough surface with a calcium coating of 2.4 µg/mm².
Figure 7:
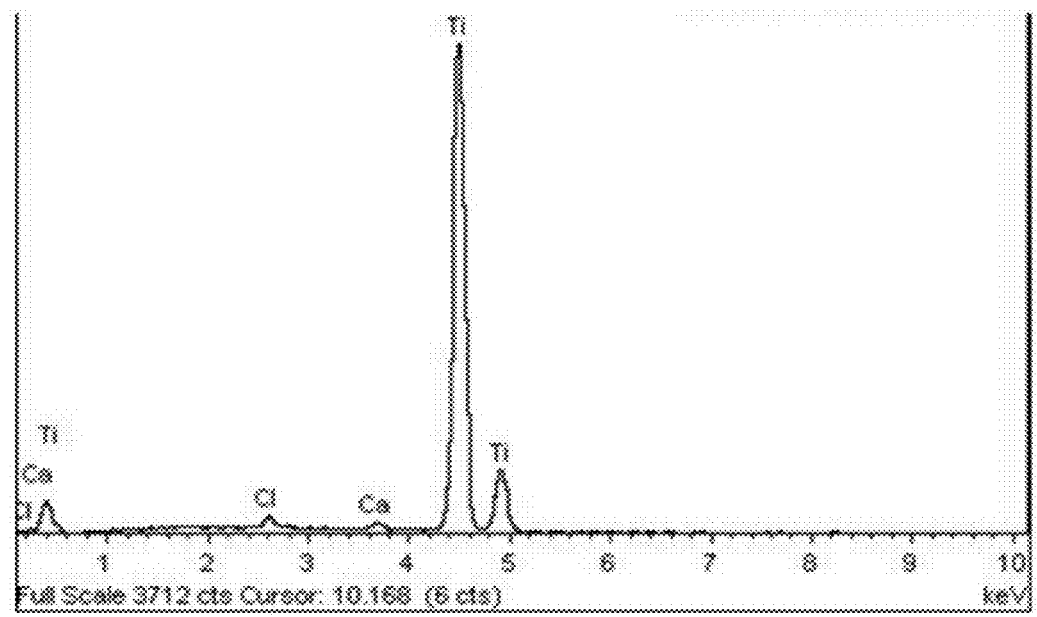
FIG. 7 shows the dispersion spectrum obtained from a rough surface with a calcium coating of 2.4 µg/mm² after immersing the surface in polar liquid.

The compositional analysis of the calcium-provided surfaces reveals the presence of salt on the surface (FIG. 6). The Ca/Cl ratio correctly corresponds with the composition of the salt ($CaCl_2$), there being approximately double the amount of Cl than Ca. After washing, and as revealed by the electron microscope (FIG. 4), it may be seen how most of the salt has disappeared from the surface (FIG. 7) and has moved to the polar medium in which it has been immersed. This is the required effect for initiating the coagulation on the surface in the event that the polar liquid to which the surfaces are exposed is blood or plasma (see Test 4). However, a small amount is still detected by EDS, a result that coincides with that previously obtained by means of XPS (X-Ray Photo-Spectroscopy, see Ellingsen J E, 1991 Biomaterials) and which confirms the presence of an amount of calcium on the surface, which may be beneficial for subsequent stages of the biomineralisation (see Test 5).

Figure 5:
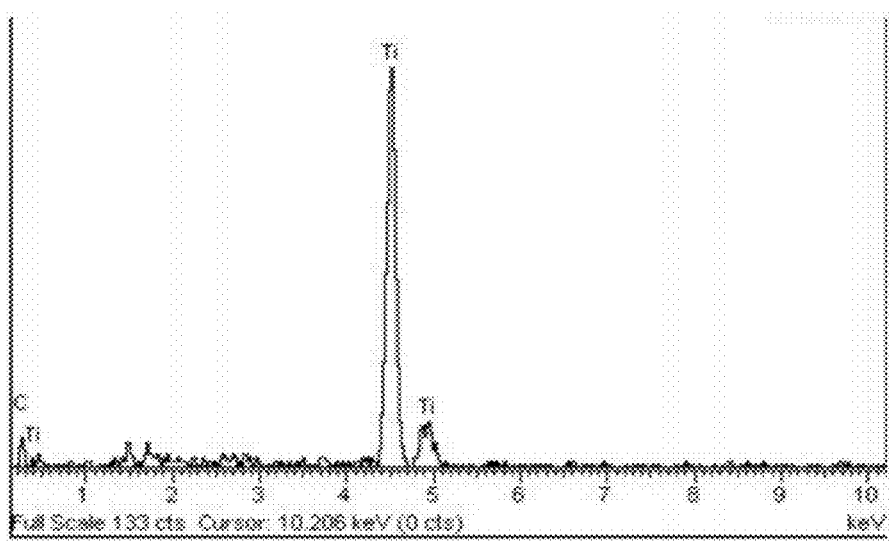
FIG. 5 shows the dispersion spectrum obtained from a rough surface that is not coated with calcium.

On another hand, the absence of carbon peaks in the spectrums of the surfaces treated with calcium, washed or otherwise (FIGS. 6 and 7), indicate that treatment with calcium after cleaning prevents contamination through the adsorption of hydrocarbons in the atmosphere, which occurs in samples that have not been treated with calcium (FIG. 5).

This test has helped determine the morphology of the coatings, and also measure their composition before and after being exposed to polar liquids. The results of this test are very useful in also analysing the results of Tests 3, 4 and 5.

Test 3: Hydrophilicity and Protection Against Contamination

1. Objective

The objective of the third test was to determine the variation of the contact angle, as a function of the amount of calcium retained by the implants and the prevalence of surface calcium depending on time and different washes.

2. Materials and Methods

All the reactives used were obtained from Scharlab S. L., Barcelona, Spain.

The surfaces of the implants were prepared using discs with a diameter of 12.7 mm, a height of 1 mm and a roughness of Sa=0.7 µm and Sdr=35%. Said discs were ultrasound-washed with Triton X-100, acetone and ethanol, for 20 minutes. Eight discs were used for each of the concentrations of base solutions.

The solutions were prepared. $CaCl_2.2H_2O$ (dihydrate) was used as a solute. 95 wt. % Ethanol was used as a solvent.

To create the coatings, the equivalent volume was deposited to that carried away by similar implant surfaces in order to provide final concentrations of 0.2, 0.7, 1.4, 2.4 and 2.9 µg/$mm^2$.

Three samples of discs were then separated: a) a first sample not to be exposed to washing, to be used in order to determine the influence of air-exposure time in the contamination of the surface and its potential loss of hydrophilicity; b) a second sample, which was exposed to a gentle wash (immersed three times in deionised water); c) a third sample, which was exposed to an intense wash (ultrasound washing for five minutes).

After coating with the solutions, the discs were then dried, being exposed to 65° C. in a vacuum stove for 1 hour. The discs were exposed to air for one and three days, to measure their stability over time.

A KSV Theta T-200 optical tension meter (Attension®, Helsinki, Finland) was used to measure the contact angle. An average of the measurement of the left and right contact angle after 30 seconds of exposure was taken.

3. Results and Discussion 3.1 Influence of the Treatment Time

The influence of the incubation time of each disc in the base solutions at different concentrations in the contact angle was measured for rapid-immersion treatment times (5 seconds), immersion for three hours and immersion for 50 days. The results (not shown) show that there are no significant differences in relation to the incubation time in the base solutions, as a result of which a common protocol of rapid immersion for 5 seconds and stove drying, as described in the methods, was adopted.

3.2 Protection Against Contamination

Figure 8:
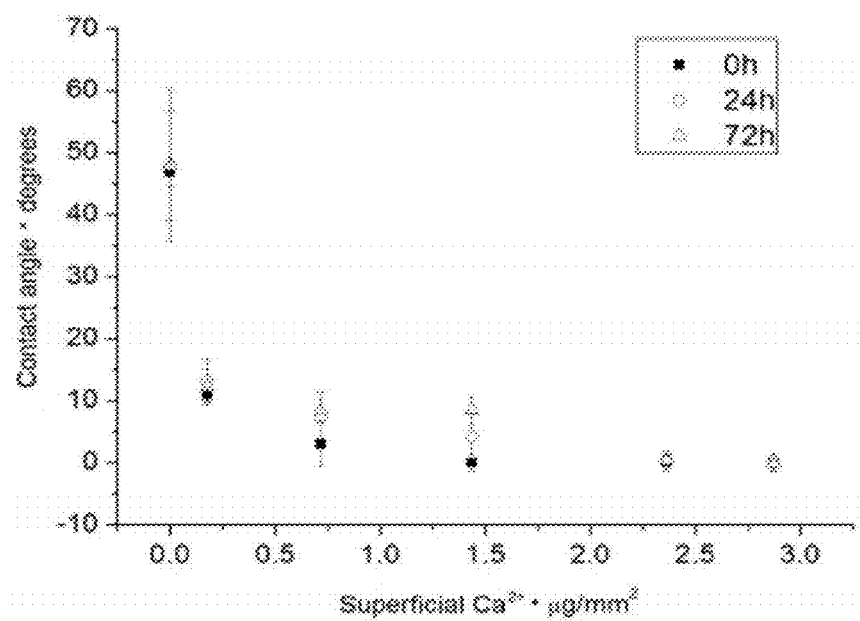
FIG. 8 shows the variation in degrees of the contact angle, as a function of the amount of $Ca^{2+}$ on the surface and the exposure time.

Following the creation of the coatings, the surfaces were left exposed to air for different periods of time in order to assess the effect of the exposure of the coatings to the atmosphere and to determine a potential loss of hydrophilicity due to the incorporation of hydrophobic particles suspended in the air. FIG. 8 shows the variation of the contact angle in degrees as a function of the amount of surface $Ca^{2+}$ and the exposure time. The results show that the contact angle barely changes if the surfaces are exposed to environmental contamination for one to three days. In other words, the test showed that the surface calcium deposit prevents hydrophobisation due to contamination through hydrocarbons in the atmosphere (see also Test 2, on the elementary composition of the surface with and without calcium).

3.3 Stability of the Calcium Deposit

After being coated and dried, the discs were exposed to two types of cleaning in water. The objective was to determine whether, after washing, enough surface calcium would remain to maintain the hydrophilic conditions of the original coating. For this reason the discs were exposed to a gentle wash, involving their immersion three times in demineralised water, as well as an intense wash, in which they were exposed to ultrasound cleaning for 5 minutes.

Figure 9:
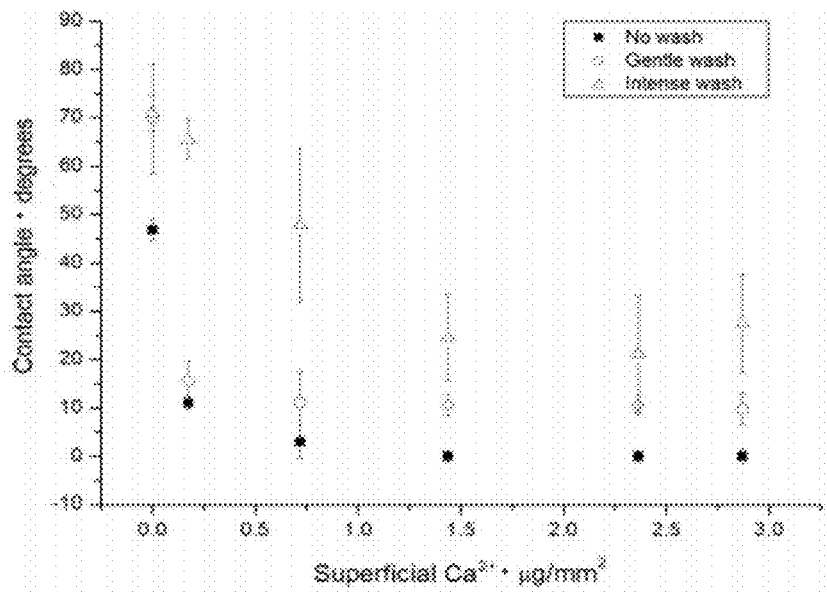
FIG. 9 shows the variation in degrees of the contact angle, as a function of the amount of $Ca^{2+}$ on the surface and the washing method.

FIG. 9 shows the variation of the contact angle in degrees according to the amount of surface $Ca^{2+}$ and the washing method. As can be seen:

In the unwashed discs (square symbols in the figure), from 0.7 μg/mm² of calcium per surface unit, the coating provides the surface with a superhydrophilic characteristic (contact angle <5°).

In the discs exposed to a gentle wash (circular symbols in the figure), simulating the conditions of the immersion of the implant in another polar liquid (water, plasma, blood) in which part of the surface calcium may be diffused in the medium and, therefore, become detached from the surface, it is seen that the contact angle increases in relation to the unwashed surfaces but remains in extremely hydrophilic conditions (<20°) compared to the uncoated reference sample.

In the discs exposed to an intense wash (triangular symbols in the figure), simulating extreme conditions, with 5 minutes of ultrasound washing, the measurement of the contact angle never drops below 20°, which did occur with gentle washing, even with the coating with least calcium. It seems logical this type of cleaning eliminates a sufficient percentage of the calcium coating to lead to a significant increase of the contact angle. From 1.4 μg/mm², however, intense cleaning does not seem to affect the excess and the contact angle remains in the 20-30° range. Nevertheless, it should be pointed out that even ultrasound cleaning is unable to change the fact that the calcium surfaces are more hydrophilic than surfaces that do not have calcium. It can be assumed that a non-insignificant amount of coating remains in the cavities of the rough surface.

In the case of the reference samples, which are calcium-free, the difference between angles of contact is due to the fact that the last stage before the drying and the measuring of the contact angle was water in the case of "washed" samples and ethanol in the case of "unwashed" samples. This latter solvent provides a greater degree of surface hydroxylation, hence the decrease in the contact angle in these types of samples.

Therefore, as regards hydrophilic properties, the test showed that the properties of implants treated according to the methods described remain substantially more hydrophylic than the untreated ones, even after being exposed to extreme mechanical cleaning processes.

Test 4: Pro-Coagulant Characteristic

1. Objective

The objective of the fourth test was to determine which amounts of calcium per surface unit enable the initiating of blood plasma coagulation. For this purpose, the range of concentration of calcium in plasma that is most suitable for causing volume coagulation (with no surface) was determined; then, which surface calcium concentration ranges stimulate coagulation, this time in the presence of the surface, were determined. Additional sodium-based surface treatments (NaOH and NaCl) were also studied, to confirm their non-pro-coagulant nature.

2. Materials and Methods

All the reactives used were obtained from Scharlab S. L., Barcelona, Spain.

Blood plasma was prepared by extracting blood from three healthy patients. A technique similar to the one described in patent EP1066838B1 was applied to obtain a Plasma Rich in Growth Factors (PRGF): the blood was centrifuged for eight minutes at 460 G; the column of plasma was then separated from the red globules and white globules by manual pipetting (unlike the protocol described in EP1066838B1, in this case, due to the criteria of volume for carrying out the experiments, the entire plasma column was selected, not merely the part richer in platelets). Both the red globules and the white globules were discarded.

For the purpose of determining which ranges of calcium concentration in the solutions are capable of initiating the coagulation of the plasma and as a prior step to modifying the surfaces with said solutions, the degree of coagulation as a function of the volume concentration of calcium was measured as follows:

a) Coagulation as a Function of the Volume Concentration of Calcium

For the purpose of determining the ranges of concentration of calcium ions in plasma at which coagulation is initiated, 10 μl of $CaCl_2$.EtOH were placed in concentrations of between 28 and 2000 mM in the bottom of a multi-well plate comprising 96 wells. The content of the wells was allowed to dry (i.e. the evaporation of the ethanol took place and was followed by autohydration), the wells then being filled with 200 μl of plasma to produce final concentrations of 1.3, 2.5, 12.5, 22.8, 45.6 and 100 mM of calcium in plasma. For the positive control (Ctrl +), prior to its placing in the plate, 10 μl of 10 wt. % of calcium hexahydrate was mixed in 200 μl of plasma (for a final concentration of 22.8 mM) and was then placed in the control wells. The negative control (Ctrl −) was prepared in the same way but without being activated with 10 μl of 10 wt. % of calcium hexahydrate. Eight replica samples were used in each case. Absorbance was measured immediately in the manner described hereafter.

b) Coagulation in the Presence of Surfaces with or Without Calcium

First of all, the surfaces were prepared. For the study of the coagulation, in which the excess surface calcium was to be measured, hollow tubes were used to enable the reader beam to move longitudinally. The tubes had a diameter of 6 mm, walls measuring 1 mm and were provided with a roughness of Sa=0.7 μm and Sdr=35%. They were ultrasound-washed with Triton X-100, acetone and ethanol, for 20 minutes. Eight tubes were used per concentration.

The solutions were prepared. Firstly, calcium solutions were prepared with $CaCl_2.2H_2O$ (dihydrate) solute and the solvents 95 wt. % Ethanol and demineralised water. Secondly, an 50 mM NaOH solution was prepared in demineralised water and a 0.9 wt. % NaCl isotonic solution.

The tubes were then exposed to a rapid immersion (5 seconds) in wells containing 1 ml of the calcium chloride solutions at the different concentrations that were being studied. Following immersion, the tubes were dried by having them exposed to 65° C. in a stove under vacuum for 1 hour. Tubes treated with NaOH and NaCl were exposed to said solutions and used immediately, without being left to dry, just as they are used in their commercial versions.

The tubes in the wells were each filled with 140 μl of plasma with the assistance of a multi-pippete. The positive and negative controls were prepared in the same way as in the measurement in volume, but this time with the tubes in the wells. In addition, the amount of 10 wt. % of calcium hexahydrate used for the positive control was chosen according to the volume of plasma (140 μl), i.e. 7.4 μl.

Immediately after the tubes were filled, absorbance (optical density) was measured with a spectrophotometer at a wavelength of 450 nm. The measurement temperature was 37° C. and recordings were made every minute of measurement for 100 minutes. The results were normalized with respect to the positive control (degree of coagulation of the control=1).

3. Results and Discussion

The complete kinetic coagulation curves (not included due to the complexity of their comparative study) show that there is a period of latency of five to ten minutes in which absorbance remains unchanged, equal to its start value (0), and that from a certain point the value increases gradually over time as the fibrin network forms and densifies as part of the coagulation process. This gradual cross-linking gradually blocks the passage of the reader beam, the absorbance therefore increasing. The absorbance value stabilises about 30 minutes after the start of the process, which indicates that the process has come to an end. It is at this point that the absorbance (optical density) values are collated so that comparisons can be made between the various samples.

Figure 10:
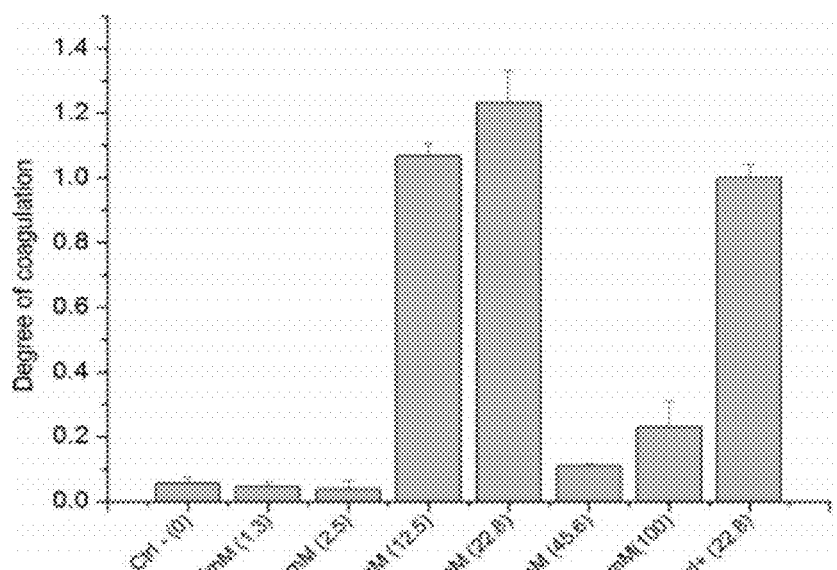
FIG. 10 shows the final degree of coagulation in volume, normalized with respect to the positive control, as a function of the amount of calcium available. The final concentration of calcium in the plasma is shown in parenthesis.

FIG. 10 thus shows the final degree of coagulation in volume (without surfaces) normalized with respect to the positive control (Ctrl +=1), according to the amount of calcium available (the final concentration of calcium in the plasma is given in brackets). The graph shows that within the range of concentration of calcium in plasma between 2.5 and 45.6 mM, the degree of coagulation is sometimes even greater than that of the positive control.

Figure 11:
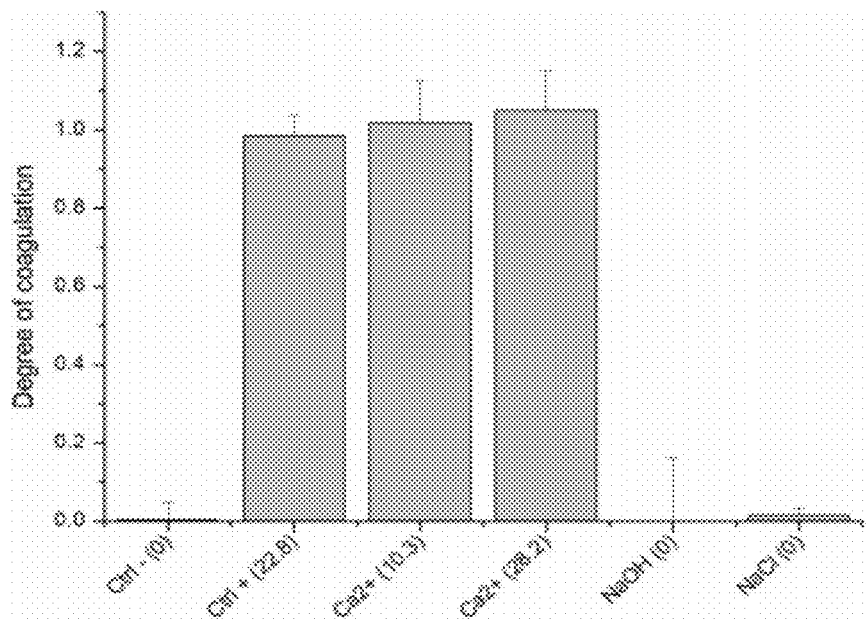
FIG. 11 shows the final degree of coagulation, normalized with respect to the positive control, as a function of the various surface treatments. Shown in parenthesis is the theoretical concentration of calcium in the plasma if all the calcium on the surface diffuses in the plasma to cause coagulation.
Figure 12:
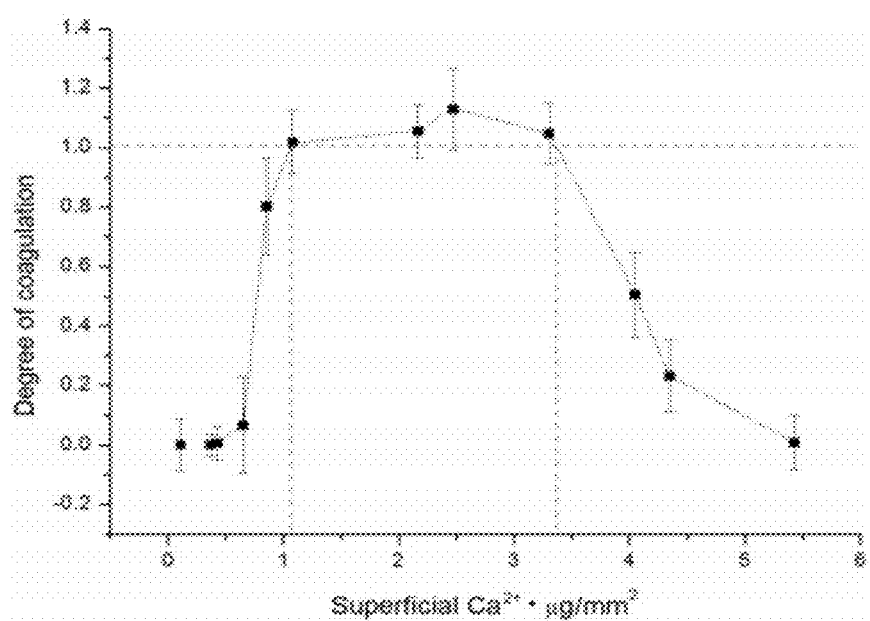
FIG. 12 shows the final degree of coagulation, normalized with respect to the positive control, as a function of the amount of surface calcium.

FIG. 11 shows the degree of coagulation inside the titanium tubes normalized with respect to the value of the positive control, as a function of the various surface treatments (provided in parenthesis is the theoretical concentration of calcium in the plasma if the samples contained surface calcium and supposing all the surface calcium had been freed into the plasma to produce coagulation). The graph shows the degree of coagulation inside the tubes once the coagulation process has ended, should it have taken place. FIG. 12 also shows the degree of coagulation solely for the case of calcium surface coatings at different surface concentrations.

FIGS. 11 and 12 shown the same experiment as FIG. 10, but with measurements having been taken with the calcium incorporated into the surfaces. NaOH and NaCl surface modifications available on the market were also studied, as a means of ascertaining whether they are capable of promoting surface coagulation (FIG. 11). The positive control was carried out in the same way as on the preceding occasion: 10 wt. % of calcium hexahydrate mixed with plasma at 22.8 mM and deposited in the well (with an untreated surface).

In the case of surfaces with no calcium (negative control, NaOH and NaCl) the lack of coagulation is evident. In the case of surfaces with calcium, the coagulation process is greater or smaller in a certain calcium concentration range. Specifically, a concentration of 0.52 μg/mm$^2$ is insufficient to cause coagulation, whereas in the range from 0.7 to 3.5 μg/mm$^2$ an even greater signal is obtained in some cases than in the positive control. From 1 μg/mm$^2$, the degree of coagulation obtained by surfaces with calcium is at least the same as the degree of coagulation of the positive control (i.e. at least 1) and this value does not seem to increase significantly in the range 1-3.5 μg/mm$^2$. However, from 3.5 μg/mm$^2$ there is a decrease in the degree of final coagulation until, from 5 μg/mm$^2$, the coagulation process is completely inhibited.

In short, this test has corroborated in surface what is known in volume, in other words that there is a range of surface calcium concentrations that initiate an ideal coagulation process but that outside this range coagulation does not occur. As they lack calcium, commercial coatings based on NaOH and NaCl, are also unable to encourage coagulation.

Test 5: Pro-Mineralising Characteristic

1. Objective

The objective of this test was to evaluate the capability of calcium phosphate phases being formed in samples exposed to a calcium surface treatment, in order to determine the ability of the surfaces to stimulate the generation of apatite.

2. Materials and Methods

All the reactives used were obtained from Scharlab S. L. Barcelona, Spain.

The surfaces of the implants were prepared using discs with a diameter of 8 mm, a height of 3 mm and a roughness of Sa=0.7 μm and Sdr=35%. Said discs were ultrasound-washed with Triton X-100, acetone and ethanol, for 20 minutes. Measurements were taken at different points of three different discs per type of surface (with calcium, without calcium).

The calcium solution was prepared. $CaCl_2.2H_2O$ (dihydrate) was used as a solute. 95 wt. % Ethanol was used as a solvent.

To create the coatings, a volume equivalent to that carried away by similar surface implants to provide a final concentration of 2.4 μg/mm$^2$ was deposited.

For the electrochemically-assisted deposition (ECAD) of calcium phosphate phases, a combined PGSTAT T302N potentiostat/galvanostat (Metrohm Autolab B. V., Utrecht, Holland) was used. This equipment was attached to a jacketed electrochemical cell to ensure a constant temperature of 36±1° C. during the electrolysis. The working electrode was configured as the cathode and polarisation took place in galvanostatic mode. For the experiment, a current density of −15 mA/cm$^2$ was applied to each sample for 30 minutes. The electrolyte used for the deposition of calcium phosphate phases was prepared with concentrations of 1.66 mM of $CaCl_2$ and 1 mM de $NH_4H_2PO_4$. The pH of the electrolyte was adjusted to 6.4 with $NH_4OH$.

Following the mineralisation treatment, the samples were rinsed five times in demineralised water to eliminate all labile residues and were left to air-dry prior to their subsequent analysis.

To assess the mineralisation of the samples a Fourier FTIR Nicolet® 6700 FT-IR transform infrared spectrometer (Thermo Fisher Scientific®, Waltam, USA) with an ATR (attenuated total reflectance) module for thin coatings was used. A total of 32 scans per sample were carried out at five different points of each sample to check the homogeneity of the coating.

3. Results and Discussion

Figure 13:
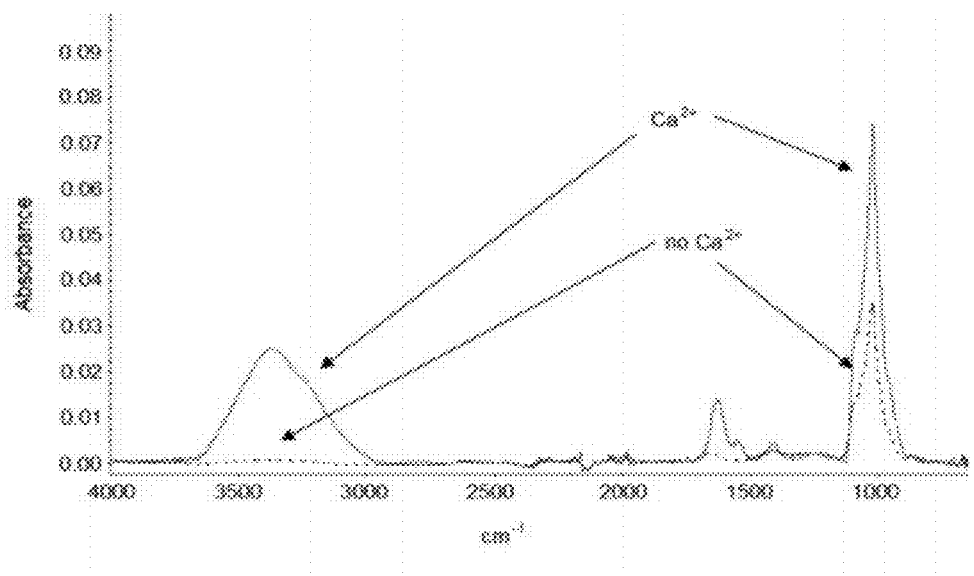
FIG. 13 shows the infrared spectrum of a sample treated with calcium (2.4 µg/mm²) and of a sample without surface calcium, exposed to electrochemically assisted deposition of calcium phosphate phases.

The roughness of the samples and the thinness of their calcium phosphate coating made it impossible to extract a sufficient amount of sample in order to carry out the analysis on KBr pellets. It is for this reason that the ATR method was used. In the present case, the lack of information in the 400-600 $cm^{-1}$ range due to the use of the ATR method is not relevant as both coatings are formed with hydroxyapatite. FIG. 13 shows the infrared spectrums of the samples with calcium and the samples without calcium. The splitting of the phosphate absorption peak ($v_3$ in 1020 and 1090 $cm^{-1}$), and the hump at 965 $cm^{-1}$, are characteristics of hidroxyapatite. The small peak at 875 $cm^{-1}$ is attributed to the replacement of carbon in the crystalline network, which indicates that it is a carbonated hidroxyapatite. The peak at 1420 $cm^{-1}$ is also an indicator of this type of hidroxyapatite. Although carbonated hidroxyapatite was obtained in both samples, in the case of the samples with calcium, the greater intensity of the peaks shows that these coatings are capable of causing the increased deposition of apatite in the same experimental conditions. The coatings with calcium also generated a far more hydrated hidroxyapatite, with the hydroxyls' characteristic manner of vibrating becoming very pronounced at around 3400 $cm^{-1}$. In addition to the greater intensity of the peaks, another aspect that should be pointed out in the case of samples with calcium is the presence of additional peaks of the carbonated hidroxyapatites (1460 and 1550 $cm^{-1}$) and the hydrated hidroxyapatites (1630 $cm^{-1}$), which are not present in samples without calcium.

In short, this test showed that discs treated beforehand with calcium are capable of producing a quicker deposition of hidroxyapatite on the surface than untreated discs, in the same experimental conditions.

Test 6: Cytotoxicity

1. Objective

The objective of the sixth test was to biologically evaluate toxicity of the coatings with calcium after 24 hours of contact with hFOB 1.19 cells, in accordance with the standard UNE-EN ISO 10993-5:2000.

2. Materials and Methods

A cell culture was grown. The hFOB 1.19 cell line (ATTC CRL 11372) was cultivated in DMEM-F12 (Invitrogen 11039-021) completed with 10% foetal bovine serum, 1% Penicillin-Streptomycin, 1% Glutamine, and 0.3 mg/mL de G418.

The surfaces were prepared in the form of discs with a diameter of 6 mm, a height of 3 mm and a roughness of Sa=0.7 µm and Sdr=35%. They were ultrasound-washed with Triton X-100, acetone and ethanol, for 20 minutes. Five discs were used per concentration.

The solutions were prepared using $CaCl_2.2H_2O$ (dihydrate) as a solute and 95 wt. % Ethanol as a solvent.

The coatings were created: for each of the concentrations the equivalent volume to that carried away by similar surface implants was deposited on the calcium-coated discs to provide final concentrations of 0.36, 1.79 and 3.26 µg/mm².

As regards the handling of the samples, all of them were exposed to β 25-50 kGy sterilisation. As a negative control PVC test tubes were used and as a positive control high-density PE test tubes were used. The controls were sterilised using ethanol. In sterile conditions, the samples were placed in the 96-well plates, with the cells later being added.

As regards the cell line and the performing of the test, the cells of the hFOB1.19 cell line were grown and a cellular suspension was obtained. 1.5×104 cells were spread in the medium/well on top of the study samples. The plate was incubated for 24 hours at 37° C. and 5% $CO_2$. Five replicas were used for each sample/control and one replica for each sample/control as a "blank" (a growth medium without cells) for the purpose of determining the background signal of each sample/control. At the end of the contact time, the number of cells/samples was measured by means of the WST-1* test. In doing so, 10 µl of WST-1/well was added and incubated for four hours (37° C. and 5% $CO_2$, darkness). Finally, the medium was removed from each well to another plate and the absorbance of the plate at a wavelength of 450 nm was read by an absorbance plate reader.

To find out the number of cells/sample, a curve was formed linking the number of known cells with the absorbance obtained by means of the WST-1 method. The WST-1 method is a colorimetric method that detects the mitochondrial activity of the cells.

As for the valuation of the test, the results were based on the quantitative evaluation of the cultivation after 24 hours of contact. The percentage cell viability for each sample tested in comparison with the results obtained for the positive control was obtained.

Relative cell viability(%)=No of sample cells/no of control cells(+)×100

The results were processed statistically by applying Student's statistical t-test to check if the differences with regard to the positive control were statistically significant or not (p<0.05).

3. Results and Discussion

Figure 14:
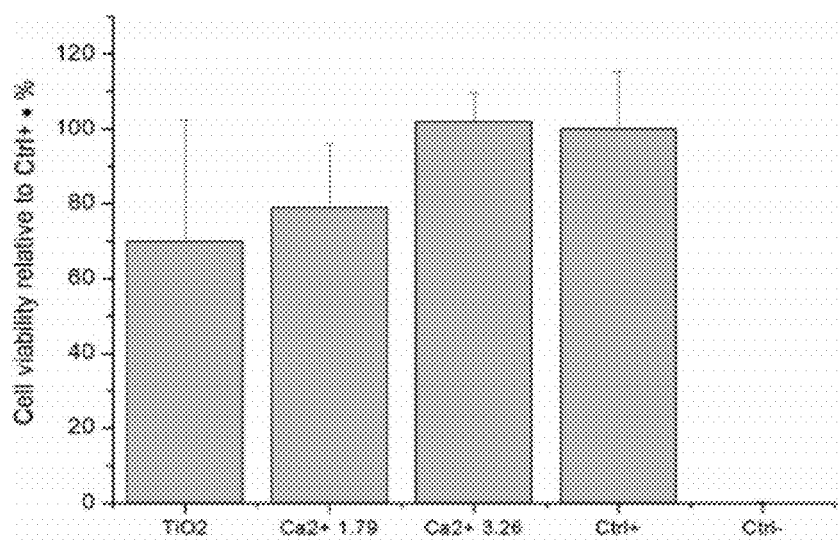
FIG. 14 shows the cellular viability relative to the positive control, following 24-hour exposure to surfaces without calcium ($TiO_2$) and with calcium (1.79 and 3.26 µg/mm²).

FIG. 14 shows the results of the cytotoxicity test in accordance with the standard UNE-EN ISO 10993-5:2000, showing in particular the cell viability relative to the positive control following 24 hours of exposure to the surfaces without calcium ($TiO_2$) and with calcium (1.79 and 3.26 µg/mm²). None of the surfaces assessed is cytotoxic for the osteoblastic cells used, as no statistically significant differences were found between the results of the positive control and the samples and none of them exceeded the cytotoxicity threshold (70% of relative viability). The surface calcium deposit does not seem to have negative effects on cellular adhesion and its viability after 24 hours of the cells being cultivated. As they are highly hygroscopic coatings, there could be a concern that these surfaces may break the cell walls when they are exposed to high osmotic pressure. There could also be a reason to believe the membrane receptors may be saturated due to excess calcium. This test rules out such effects. In particular, the high hygroscopicity of the calcium coating means that it hydrates quickly with water molecules from the environment, with the result that at the point of contact with the cells and the cell medium, the osmotic gradient drops to harmless levels in terms of cell lysis.

Test Conclusions

The present invention allows homogeneous calcium coatings to be obtained on titanium substrates with very little dispersion in its surface distribution. The solvent's gathering of calcium salts is almost immediate and does not increase with the exposure time but with the solute concentration in the solvent. The hygroscopic characteristic of calcium chloride allows a hydrated layer to form on the surface, which prevents the "hydrophobising" effect due to the atmospheric contamination of the titanium oxide by hydrocarbons in the atmosphere. This protection lasts over time. In addition, these coatings provide the surfaces with a superhydrophilic nature based on relatively low concentrations of calcium ions per surface unit. Slight losses in hydrophylicity are only observed when very heavy washes are carried out, and even then the surfaces have a more hydrophylic characteristic than those not originally covered with calcium. A specific characteristic of these coatings is that they may be dissolved in the presence of polar liquids such as blood or plasma. As calcium is a basic component in the coagulation cascade and its triggering, the main characteristic of the surfaces is that they cause coagulation when coming into contact with the aforementioned biological fluids. This process is dependent on the concentration of calcium and, as a result, this document specifies a range of surface concentrations of calcium in which coagulation takes place in an optimal manner: in the case of treatment with $CaCl_2$, from 0.70 to 3.5 µg/mm² or base solution concentrations of between 100 and 1000 mM. The study of the mineralising ability (pro-mineralising characteristic) shows the calcium coatings have a greater capability to form apatite than the non-coated surfaces. Finally, the cytotoxicity study rules out any negative effect of these coatings on osteoblastic cells.

The invention claimed is:

1. A method for modifying the surface of an implant, comprising the step of storing the implant in a container that contains a solution of at least one polar-liquid-soluble calcium salt, the implant being stored in contact with said solution and insulated from the outside, where the concentration of the solution of at least one polar-liquid-soluble calcium salt is between 20 and 2000 mM.

2. The method according to claim 1, wherein a solute of the solution of at least one polar-liquid-soluble calcium salt is calcium chloride and the concentration of calcium chloride in the solution is between 100 and 1000 mM.

3. The method according to claim 1, wherein a solute of the solution of at least one polar-liquid-soluble calcium salt is calcium chloride and the solvent is demineralised water.

4. The method according to claim 1, wherein a solute of the solution of at least one polar-liquid-soluble calcium salt is calcium acetate and the solvent is demineralised water.

* * * * *